United States Patent [19]

Sanger et al.

[11] Patent Number: 5,452,082
[45] Date of Patent: Sep. 19, 1995

[54] FLOW CELL WITH LEAKAGE DETECTION

[75] Inventors: Robert J. Sanger, Park Ridge; Stephen M. Metro, Chicago, both of Ill.; Brian K. Masterson, Placerville, Calif.

[73] Assignee: UOP, Des Plaines, Ill.

[21] Appl. No.: 270,720

[22] Filed: Jul. 5, 1994

[51] Int. Cl.⁶ ............... G01N 21/05; G01M 3/04
[52] U.S. Cl. ................. 356/246; 356/440
[58] Field of Search ............ 356/246, 410, 440

[56] References Cited

U.S. PATENT DOCUMENTS

| | | | |
|---|---|---|---|
| 4,008,397 | 2/1977 | Zdrodowski | 250/373 |
| 4,260,257 | 4/1981 | Neeley et al. | 356/246 |
| 4,540,280 | 9/1985 | Anderson et al. | 356/246 |
| 4,588,893 | 5/1986 | Vidrine et al. | 250/428 |
| 4,988,155 | 1/1991 | Harner et al. | 356/440 X |
| 5,003,174 | 3/1991 | Datwyler et al. | 356/246 X |
| 5,074,663 | 12/1991 | Winterton et al. | 356/246 X |
| 5,078,493 | 1/1992 | Evens et al. | 356/246 |
| 5,120,129 | 6/1992 | Farquharson et al. | 356/440 X |
| 5,140,169 | 8/1992 | Evens et al. | 250/576 |

Primary Examiner—Vincent P. McGraw
Attorney, Agent, or Firm—Thomas K. McBride; John G. Tolomei

[57] ABSTRACT

A flow cell for fiber optics spectroscopy having a radiation transparent window for the transmission of radiation uses a dual O-ring arrangement to prevent leakage of a medium undergoing evaluation around the window and a vent for indicating leakage between the O-rings. The arrangement also provides for the use of an O-ring to urge the window against a retainer that holds a lens to direct radiation into the window. Biasing of the window against the lens retainer and the use of a radial O-ring arrangement allows precise control of the separation between windows in the total path length for radiation travel across a fluid sample.

2 Claims, 2 Drawing Sheets

FLOW CELL WITH LEAKAGE DETECTION

FIELD OF THE INVENTION

This invention generally relates to spectrophotometric detectors for measuring radiation a radiation source via a sample cell and a photo-detector which measures the radiation absorbance. More specifically, this invention relates to the arrangement of flow cells that contain the sample through which the radiation passes and is measured by means of fiber optic cables.

BACKGROUND OF THE INVENTION

The use of spectrophotometry has been applied to a wide range of materials to determine properties by measuring the adsorbance of radiation across a sample in a fluid cell. In such fluid cells one or more radiation transparent optical windows allow radiation to pass through the fluid sample contained in the cell and to pass through a detector. In the most common flow cell arrangements, radiation passes through an entrance window, a fluid sample and an exit window on its way to a detector as the fluid sample flows through the cell. The flow cells typically include a lens to focus radiation on the window in a desired pattern. The direction of radiation transmission and detection may be parallel to the flow of fluid through the cell or radiation and fluid may have a crossflow arrangement. Parallel and cross-flow arrangements for cells are disclosed in U.S. Pat. Nos. 4,192,614 and 5,078,493 the contents of which are hereby incorporated by reference.

Two important considerations in the arrangement of flow cells are the prevention of sample leakage around the radiation transparent window and control of the flow path length for the radiation across the sample. Leakage detection is particularly important when monitoring hazardous or corrosive fluids. Corrosive fluids pose additional difficulties on the operation of flow cells since any leakage of such fluids may impair the operability of the flow cell. U.S. Pat. No. 5,078,493 provides an O-ring between the corrosive environment of the fluid sample and the remainder of the flow cell containing the fiber optic cable lens and a sapphire window. The O-ring is made of materials that can resist the attack of highly corrosive substances such as hydrogen fluoride, hydrogen chloride or strong caustics. This arrangement uses a single O-ring in an axial or crush design wherein axial displacement of the sapphire window through the O-ring provides pressure for the O-ring seal. This arrangement provides a sealing element that can resist highly corrosive atmospheres and immediately indicates when a seal failure has occurred. Leakage of sample fluid between the lens and window or fiber cable and lens can interfere with the operation of the flow cell device and yield faulty measurements. Accordingly, there is a need for a flow cell having a seal arrangement that performs reliably and immediately indicate when any failure of the seal said has occurred.

In addition, there is a need for a flow cell that is easily manufactured and assembled while yet providing precise control of the radiation flow path length across the fluid sample. The axial or crush design of the seal disclosed in U.S. Pat. No. 5,078,493 interferes with the control of the radiation path length across the sample since the amount of pressure exerted on the O-ring will vary the displacement of the window relative to the sample.

It is an object of this invention to provide a flow cell arrangement that maintains seal integrity while warning of potential leakage.

It is a further object of this invention to provide a flow cell arrangement that improves control of the radiation path length across a fluid sample.

BRIEF SUMMARY OF THE INVENTION

This invention is a flow cell arrangement that isolates a section of a bore containing a radiation transparent window with an O-ring seal and an additional seal to facilitate monitoring of sample leakage across the first O-ring seal while the second seal remains intact. In this manner the invention provides detection of any leakage to prevent an uncontrolled escape of fluids from the flow cell. The seals of this invention can also be arranged to prevent fluid entry between the window and lens or lens and fiber optic cable that would interfere with radiation detection measurements and cause permanent damage to optical components. This arrangement makes the flow cell particularly advantageous for avoiding leakage in the monitoring of corrosive fluids. This flow cell is particularly useful in the monitoring of process stream comprising hydrofluoric acid. This invention is also highly advantageous for non-corrosive fluids where leakage detection also suggests the possible malfunction of the flow cell.

This seal arrangement and leakage detection utilizes a flow cell construction that simplifies control of radiation flow path length across the fluid sample. The arrangement permits precise control of window positioning without interfering with the sealing characteristics between the window and the flow cell. This permits the tolerance of window spacing to be controlled independent of any sealing characteristics.

Accordingly, in one embodiment this invention is a flow cell for the transmission and detection of radiation. The flow cell comprises a housing, a first bore formed by the housing and extending longitudinally through the housing for conducting or containing a fluid, a second bore formed by the housing that extends into the housing and intersects the first bore, a window disposed within the housing for transmitting radiation, a first O-ring located between the window and the second bore to provide a first seal at a first location on the second bore. Means are provided for forming a second seal at a second location of the second bore and for detecting leakage in a section of the second bore between the first and second seals.

In a more limited embodiment, this invention is a flow cell for the transmission and detection of radiation. The flow cell comprises a housing, a first bore formed by the housing and extending longitudinally through the housing for conducting a fluid therethrough and a second bore formed by and extending radially into the housing in an intersecting arrangement with the first bore. The second bore contains a window for transmitting radiation. The housing or the window forms a first O-ring groove that retains a first O-ring. The first O-ring encircles the window and is radially compressed between the window and bore. A second O-ring is spaced apart from the first O-ring and disposed between the window and the bore. Means for detecting leakage of fluid from the first bore in the section between the two O-rings is also provided.

In a more specific embodiment, this invention is a flow cell for the transmission and detection of radiation that comprises a housing block. The housing block defines a first cylindrical bore extending longitudinally through the housing for passing a fluid therethrough and a second cylindrical bore in a perpendicular and intersecting arrangement with the first bore. Windows are disposed within the second bore on each side of the first bore for transmitting radiation across the first bore. A pair spaced apart O-rings encircle each of the windows and are compressed between a window and the second bore. O-ring grooves defined by either the second bore or the window retain each of the compressed O-rings. A duct communicates a section of the second bore between each pair of O-rings with the outside of the housing.

Additional details and embodiments of the flow cell are disclosed in the following detailed description of the invention.

DETAILED DESCRIPTION OF THE INVENTION

Figure 1:
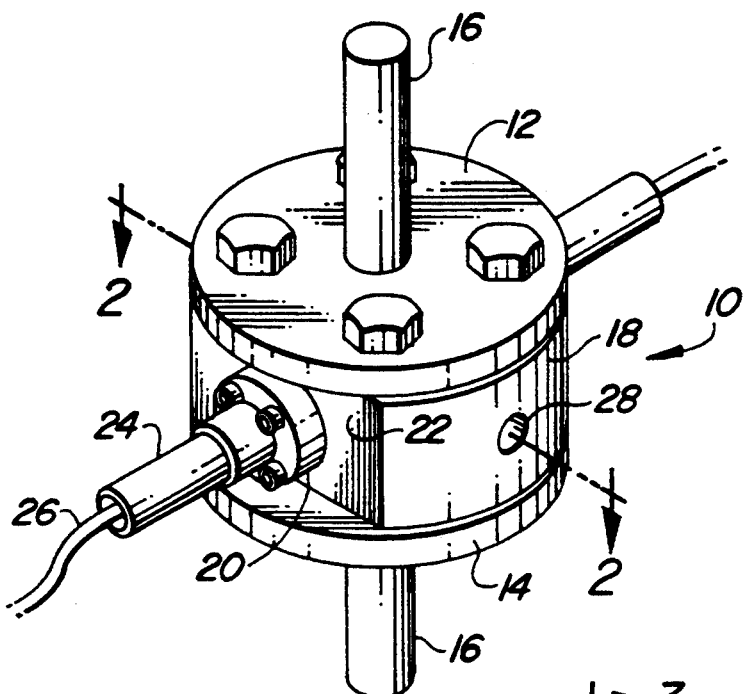
FIG. 1 is an isometric view of the exterior of a flow cell located between two flanges of a sample line.

The overall arrangement of a spectrophotometer apparatus and its method of use are fully disclosed in U.S. Pat. No. 4,786,171, the contents of which are hereby incorporated by reference. The flow cell arrangement of this invention is the particular component of the apparatus used to deliver radiation and to measure its adsorbance of the radiation across a fluid sample. In this regard the flow cell of this invention will use a fiber optic cable to deliver a light source to the flow cell and another fiber optic cable to return light to light detection components of the apparatus. The details of this invention focus exclusively on the flow cell arrangement, necessary components for connection of the fiber optic cables to the flow cell and transmission of the light source across the fluid sample. Additional details of the fiber optic cable and preferred components for the transmission of the light source are disclosed in the following detailed description of the preferred embodiment which is not meant to limit the scope of this invention to the particular details disclosed therein.

The flow cell arrangement of this invention is susceptible to many variations in arrangement. For example, the flow cell arrangement may transmit light across the fluid flow sample in a crosswise or parallel arrangement. In a parallel arrangement the second bore containing the window will lie along the axis of the first bore containing the fluid sample. All arrangements of the flow cell use a radiation transparent window to contain the sample while passing the radiation through the sample. The window can be composed of any material having suitable radiation transparency and compatibility with the fluid sample, but it is typically composed of a sapphire.

A first seal between the window and the sample provides the primary seal to maintain separation of sample fluid from optical elements of the flow cell. It is essential to this invention that a first seal be provided between the window and the sample. The first seal is provided by an O-ring is referred to as the inner O-ring since it is located closest to the fluid sample and is composed of a material that will resist the environment of the fluid sample. The O-ring may be made of any material that resists the corrosive or deteriorating effects imposed by the monitoring of particular samples. In highly corrosive environments such as a hydrofluoric acid, fluoro elastomers such as Kalrez ® are preferred. Other suitable O-ring materials for such environments may comprise chloroprene polymers. This invention is also useful in other environments having less corrosive effects and more common O-ring materials such as silicone, rubber, neoprene, etc. may be used for the O-rings. The inner O-ring may be arranged in any way that will provide an effective seal. This invention generally uses a radial arrangement for the first O-ring wherein the O-ring undergoes a controlled amount of compression between the window and the walls of the housing. In a typical radial arrangement of this type, the cylindrical walls of the housing compress the O-ring against a cylindrical groove in the window such that total compression is controlled within a range dictated by the tolerances on the cylindrical bore and the O-ring grooves. This radial arrangement permits window arrangements to be independent of O-ring compression.

The leakage detection of this invention uses a second seal to the outside of the first seal to isolate a section of the flow cell that contains the window and lens. Any means can be used to form the second seal such as washers, sealants or packing. However, the second seal will ordinarily also be formed by an O-ring in a bore that contains the window and the lens. The second seal may be located anywhere along the second bore. Preferably the second seal has a location between the bore and the windows such that it prevents leakage of the fluid sample past the first seal from interfering with other pans of the apparatus or transmission and detection of radiation through the cables, lens, and window.

Warning of any leakage beyond the first seal is provided by monitoring the section of the flow cell between the first and second seals. This monitoring may be accomplished in any way that indicates the presence of fluid or fluid leakage and includes visual indication, electrical and chemical sensing and pressure measurements. In its simplest and preferred form, this invention monitors leakage by communicating the section between the two seals with a duct that conducts any fluid leakage to the outer portion of the housing. In the case of non-hazardous fluids, the duct may permit leakage of the fluid directly onto a flange where an indicator paint or other such substance can warn of the fluid leakage past the first seal. Where any emission of a the fluid sample is undesirable, the duct will communicate with contained leakage detection indicators such as a bubbler. In the case of highly corrosive environments such as an HF alkylation process, the duct may communicate directly with an HF acid detector. Whether communicating directly with a detector or open to the atmosphere, it is also preferred that a flow restrictor be added at the outlet of the duct to limit the escape of fluid if leakage from the first seal is severe.

DETAILED DESCRIPTION OF THE PREFERRED EMBODIMENT

FIG. 1 depicts the flow cell 10 of this invention interposed between an upper flange 12 and a lower flange 14. The flanges connect the flow cell with a conduit 16 that carries a slip stream of the process fluid to be analyzed.

The flow cell consists of a housing block 18. A conduit fitting 20 is bolted to a face 22 of housing block 18.

The conduit fitting retains a light gauge, electrical type conduit 24 that protects a fiber optic cable 26. Fiber optic cable 26 extends into the cell block in a manner herein after described. Cell block 18 also has a port 28 for indicating leakage of the fluid sample past a first seal of the flow cell.

Figure 2:
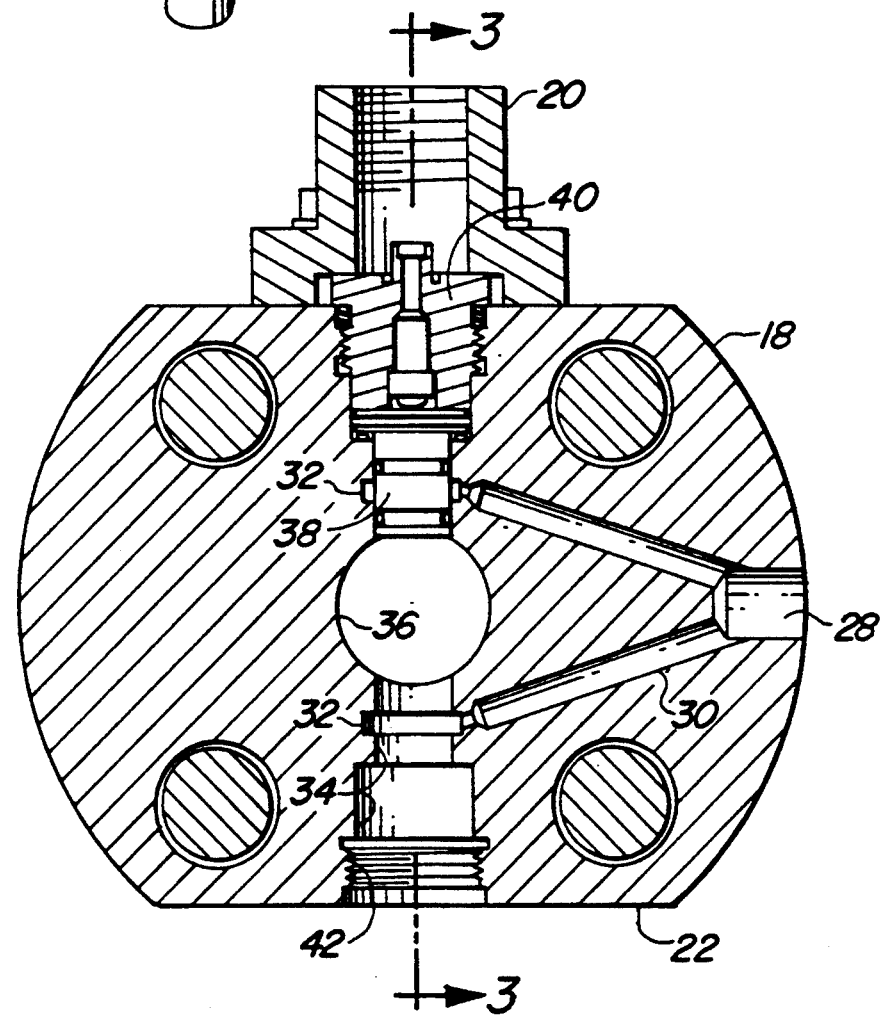
FIG. 2 is a section view taken across line 2—2 of FIG. 1 showing a preferred arrangement of the flow cell of this invention.

FIG. 2 shows orifice opening 28 communicating with a pair of ducts 30. Each of ducts 30 communicate with a groove 32 that surrounds a step bore 34 that extends radially across housing block 18 and intersects a sample bore 36. On each side of sample bore 36 step bore 34 retains a sapphire window 38 and a lens holder 40 to the outside of each sapphire window. A threaded portion 42 of bore 34 retains lens holder 40 in place. Conduit fitting 20 surrounds the outer portion of lens holder 40. Window 38, lens holder 40 and conduit fitting 18 are normally present on both sides of sample bore 36, but have been omitted from one side of FIG. 2 for clarification. Similarly, fiber optic cable 26 and conduit 24 are also omitted from FIG. 2 for clarification.

Figure 3:
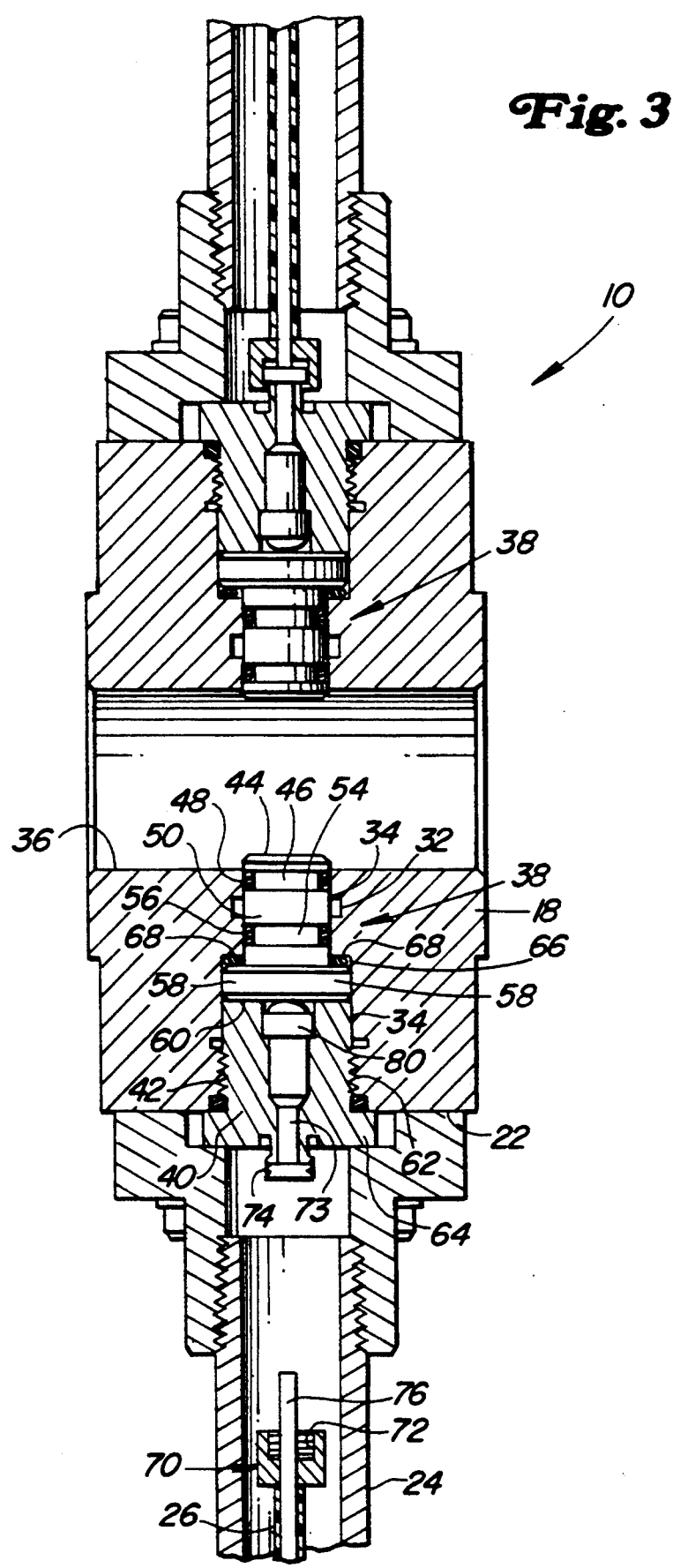
FIG. 3 is a section view taken across line 3—3 of FIG. 2.

The arrangement of window 38 lens holder 40 are more clearly shown in FIG. 3 along with conduit 24 and the fiber optic cable 26. Window 38 has a face 44 that extends approximately a 1/16th inch or less into sample bore 36. The extension of window 38 into sample bore 36 aids in preventing any fouling over the surface of the window. In other arrangements it may be desirable to have the window extend into the bore by greater distances than 1/16 of an inch to yield smaller path lengths.

A first groove 46, formed around the inside of window 38, retains an O-ring 48 between the inside of bore 34 and the window. Groove 46 has a depth that slightly compresses O-ring 48 between bore 34 and the bottom of groove 46. A land 50 separates a second groove 52 from the first groove 46 and retains a second O-ring 56 therein. The inner surface of bore 34 compresses O-ring 56 by a controlled amount set by the depth of groove 54. Any failure of the seal associated with O-ring 48 permits fluid to flow from sample bore 36 into groove 32. Ducts 30, as shown in FIG. 2, eventually communicate such leakage to orifice 28 for detection. Isolation of the flow cell and repair or replacement of the defective O-ring is then possible to prevent erroneous readings and any deterioration or harm to the other components of the flow cell.

A larger diameter portion of window 38 defined by a lip 58 extends into a large diameter portion of bore 34. Lens holder 40 backs against an outer window face 60 to urge the window towards sample bore 36. Engagement of threads 62 into threaded portion 42 of the housing block fully displaces the lens holder 40 into the housing block up a limit position controlled by a shoulder 64 that contacts face 22 of the housing block 18. Projection of lens holder 40 into bore 34 by the amount limited through shoulder 64 maintains the minimum projection of window 38 into sample bore 36. An O-ring 68 acts on a side of lip 58 opposite the lens holder to resiliently bias window 38 against the lens holder to prevent additional extension of window 38 into sample bore 36. O-ring 68 conveniently lies within a shoulder 66 of stepped bore 34. In addition to resiliently biasing the window into the lens holder, O-ring 68 may provide a yet an additional seal to prevent leakage of fluid from sample bore 36 past the window 38. Biasing windows 38 against lens holders 40 and controlling the projection of lens holder 40 toward the bore 36 with shoulder 64 facilitates the precise control of the total space between windows 38 as radiation is transmitted across bore 36.

Conduit 24 which houses the fiber optic cable 26 that supplies radiation to the windows 38. An SMA connector 70 at the end of the fiber optic cable 26 has a threaded portion 72 that engages a mating connection 74 on the outside of lens holder 40. A portion 76 of SMA connector 70 extends through a channel 78 of lens holder 40 for direction of radiation into a collimating lens 80 that directs a desired radiation pattern into window 38.

The housing forming the first and second bore preferably provides a substantial mass of material to improve the reliability and durability of the flow cell. Providing the flow cell body with a relatively large mass dampens externally imposed vibrations from sources such as connecting piping. By substantial mass it is meant that the housing preferably is constructed from a block that provides material in excess of the that required to merely define the necessary bores for the sample, window and lens. In order to provide this additional mass, the dimension of the housing perpendicular to the first and second bores is typically at least equal to the length of the second bore. In a highly preferred form the flow cell is sandwiched between two flanges of a sample line that supplies fluid to the flow cell and the flow cell will have a diameter that at least equals 80% of diameter of the flanges.

Those skilled in the art can readily appreciate that the flow cell arrangement is susceptible to a variety of variations for which no patent protection is hereby relinquished by the specific description herein as set forth in the following claims.

We claim:

1. A flow cell for the transmission and detection of radiation comprising:
   a) a housing block;
   b) a first cylindrical bore formed by said housing and extending longitudinally through said housing for passing a fluid through said housing;
   c) a second cylindrical bore formed by and extending through said housing block in an intersecting arrangement with said first bore having a step on each side of said first bore defining an inner small diameter portion and an outer large diameter portion;
   d) windows extending into the small diameter portions of said second bore on each side of said first bore for transmitting radiation across said first bore, each of said windows defining a lip that extends into said large diameter portion;
   e) a pair of annular O-ring grooves defined by and spaced apart along a longitudinal axis of each of the windows or said inner small diameter portions of said second bore;
   f) a pair of radially compressed O-rings retained by said annular grooves and encircling each of said windows with each O-ring compressed radially between a window and said small diameter portion of said second bore;
   g) a duct communicating each section of said bore between each pair of radially compressed O-rings with the outside of said housing;
   h) a longitudinally compressed O-ring disposed between said lip and said step;
   i) a lens retainer located in each large diameter portion of said second bore, each lens retainer having an inner face abutting one of said windows to bias said window toward said first bore.

2. The flow cell of claim 1 wherein each pair of said annular O-ring grooves is defined by one of said windows.

* * * * *